United States Patent [19]

Le Blevec et al.

[11] Patent Number: 5,488,190
[45] Date of Patent: Jan. 30, 1996

[54] PREPARTION OF VINYL CHLORIDE BY ULTRAPYROLYSIS OF 1,2-DICHLOROETHANE

[75] Inventors: Jean-Marc Le Blevec, Port Louis; Yves Correia, Chateau Arnoux; Jean-Jacques Masini, Chaponost; Jacques Bousquet, Irigny, all of France; Maurice A. Bergougnou, London, Canada

[73] Assignee: Elf Atochem S.A., Puteaux, France

[21] Appl. No.: 49,498

[22] Filed: Apr. 21, 1993

[30] Foreign Application Priority Data

Apr. 21, 1992 [FR] France .................. 92 04853

[51] Int. Cl.⁶ .................................................. C09C 17/25
[52] U.S. Cl. ................................................. 570/226
[58] Field of Search ...................................... 570/226

[56] References Cited

U.S. PATENT DOCUMENTS

| 1,986,876 | 1/1935 | Baxter et al. | 570/226 |
| 3,919,336 | 11/1975 | Kurtz | 570/226 |
| 4,590,318 | 5/1986 | Longhini | 570/226 |

FOREIGN PATENT DOCUMENTS

| 572902 | 5/1959 | Belgium | 570/226 |

*Primary Examiner*—Johann Richter
*Assistant Examiner*—John Peabody
*Attorney, Agent, or Firm*—Burns, Doane, Swecker & Mathis

[57] ABSTRACT

Vinyl chloride monomer is selectively prepared by intimately contacting, in the absence of steam, a feedstream of 1,2-dichloroethane with a flow of fluid or solid particulates heated to such elevated temperature and for such minim period of time, e.g., 0.010 to 0.5 second, as to flash transfer a dehydrochlorinating amount of thermal energy to the 1,2-dichloroethane and thereby ultrapyrolyzing at least a fraction of same into vinyl chloride and HCl, and recovering the vinyl chloride from the medium of ultrapyrolysis.

15 Claims, No Drawings

PREPARATION OF VINYL CHLORIDE BY ULTRAPYROLYSIS OF 1,2-DICHLOROETHANE

BACKGROUND OF THE INVENTION

1. Field of the Invention

The present invention relates to the preparation of vinyl chloride by ultrapyrolysis of 1,2-dichloroethane, and, more especially, to such ultrapyrolysis whereby the 1,2-dichloroethane is heated to an elevated temperature as rapidly as possible and, after approximately 0.1 to 0.5 second, the medium of reaction is advantageously quenched to block any further reaction.

2. Description of the Prior Art

Pyrolysis of 1,2-dichloroethane (D12) in the gaseous phase is the most widely used industrial process for producing vinyl chloride, the basic starting material for PVC. This process is described, for example, in Ullmann's *Encyclopedia of Industrial Chemistry*, 5th Edition, Volume A6, pages 287–289 (1986).

According to this process, 1,2-dichloroethane is heated in a tubular oven, on the side of the tubes, to 500° C.; the degree of conversion is 50% to 60%, the selectivity 95% to 99%, and the residence time ranges from 10 to 20 seconds.

If it is desired to increase the conversion, there is a risk of coke depositing inside the tubes. Avoiding such coke deposits by dilution of the 1,2-dichloroethane with hydrochloric acid prior to the pyrolysis is described in European Patent EP-195,719, assigned to the assignee hereof. Nonetheless, this particular pyrolysis process requires very heavy and expensive apparatus.

The article by Paouschkin and Charnaia, *Neftekhimia*, Vol. 10, part 4, pages 583–585 (1970), describes the pyrolysis of 1,2-dichloroethane in the presence of steam at a concentration of 2.5 parts of water per 1 part of 1,2-dichloroethane. The pyrolysis is carried out in a reactor, the walls of which are covered by carbon deposits, at a temperature ranging from 600° to 850° C. It is described that "once having passed through the evaporator at a temperature of 600° C., the steam and the 1,2-dichloroethane at a given rate were brought into the reactor." Then indicated is a volumetric rate of 0.73 hour$^{-1}$ ensuring a contact time equal to 0.003 seconds, which apparently is inconsistent. It is not seen how the steam/1,2-dichloroethane mixture can be conveyed through an evaporator at 600° C. and be heated to a temperature of from 600° to 850° C., all in 0.003 second. Moreover, the results demonstrate a large amount of acetylene byproduct. It is also very problematical to carry out the pyrolysis on an industrial scale in the presence of water, the separation from HCl being difficult.

European Patent Application EP-281,218 describes a hydrocarbon cracking process for the production of olefins in which a stream of particles, previously heated to a temperature of from 926° C. to 1,648° C., is contacted for 10 to 100 milliseconds (preferably 20 to 50 milliseconds), with a stream of naphtha or heavy oils, themselves heated beforehand to a temperature of from 260° C. to 690° C., into which steam is also injected (steam cracking). The ratio by weight of the particles to the stream of naphtha to be cracked ranges from 5 to 200, namely, the lowest temperature attained by the naphtha is, in the event of the particles at 926° C., naphtha preheated to 260° C., and the particles/naphtha ratio having a value of 5, at approximately 800° C.

The highest temperature attained by the naphtha is, in the event of particles at 1,648° C., of the naphtha preheated to 690° C. and the particles/naphtha ratio having a value of 200, at approximately 1,648° C. On page 24, lines 56–58, this technique is suggested for pyrolyzing 1,2-dichloroethane, at a temperature of from 800° to 1,648° C., preferably for 0.02 to 0.05 second, and in the presence of water.

If the kinetic equation of D. H. R. Barton (*Journal of Chemical Society*, page 148 (1949)) is considered, it is determined that, at 570° C. for 0.160 s in a reactor with a surface/volume ratio of 3.6 cm$^{-1}$, 2.4% of conversion of the 1,2-dichloroethane is obtained, the 1,2-dichloroethane having been diluted beforehand with nitrogen, nitrogen/1,2-dichloroethane molar ratio =10.

With a contact time of 0.050 s, a conversion of 0 (zero) % is obtained.

Moreover, it is known that, by carrying out the reaction at high temperatures, serious risk exists of producing substantial acetylene byproduct.

SUMMARY OF THE INVENTION

It has now unexpectedly been determined that 1,2-dichloroethane can be heated as rapidly as possible to a temperature of approximately 500° to 750° C. by intimately admixing it with a very hot fluid or solid particles, the 1,2-dichloroethane being maintained thereat, for example for 0.010 to 0.25 second, and then quenched, whereby a high conversion of the 1,2-dichloroethane and a very good selectivity in respect of vinyl chloride are thus attained.

Briefly, the present invention features a process for the preparation of vinyl chloride by pyrolysis of 1,2-dichloroethane in the absence of steam, comprising (i) contacting a feedstream consisting essentially of 1,2-dichloroethane, for a very short period of time, with a fluid or a stream of particles at an elevated temperature, whereby at least a fraction of the 1,2-dichloroethane is pyrolyzed into vinyl chloride and HCl, and (ii) concomitantly separating the formed vinyl chloride from the medium of ultrapyrolysis.

DETAILED DESCRIPTION OF PREFERRED EMBODIMENTS OF THE INVENTION

More particularly according to the present invention, the aforesaid contacting can be effected by any means, the crucial factor being to introduce the heat as rapidly as possible whereby the 1,2-dichloroethane is "flash" heated to a temperature such that it dehydrochlorinates into vinyl chloride and HCl. This markedly differs from the process of the prior art in which the 1,2-dichloroethane is heated in the tubes of an oven. The heat transfer to liquid 1,2dichloroethane, or gaseous 1,2-dichloroethane if it has been vaporized beforehand, and then to the gaseous 1,2-dichloroethane to heat it to 400° or 500° C. and to provide the energy of dehydrochlorination, is slow since this is a gas/gas exchange: flame or smoke/wall of the tube/1,2-dichloroethane gas.

It suffices according to the present invention to admix the feedstream containing the 1,2-dichloroethane with either a hot gas flow such as nitrogen, methane, benzene, ethylene, HCl or a flow of hot particles such as those of silica, corundum-type alumina or attapulgite silicoaluminates. The mixing is instantaneous, the temperature of the 1,2-dichloroethane is instantaneously raised, and pyrolysis is thus carried out. The size of the particles advantageously ranges from 10 to 500 microns, preferably from 10 to 40 µm.

The particles can be entrained in and transported by a fluid vehicle (transport gas).

The stream containing the 1,2-dichloroethane can be pure 1,2-dichloroethane, impure 1,2-dichloroethane or 1,2-dichloroethane together with a product which does not interfere with the dehydrochlorination (pyrolysis) of the 1,2-dichloroethane.

It is convenient and simpler to employ a stream consisting only of 1,2-dichloroethane.

The pyrolysis is carried out in the absence of water.

Although pyrolysis of the 1,2-dichloroethane begins from 400° C., the pyrolysis is carried out at a temperature of at least 480° C. and preferably above 550° C.

It is preferable not to exceed 800° C. This is the temperature attained by the 1,2-dichloroethane as soon as it is mixed with the fluid or the stream of particles at high temperature. It has been determined that a temperature ranging from 550° to 750° C., and preferably from 550° to 650° C., is well suited for the process of the invention.

The temperature then decreases as a result of the endothermic pyrolysis reaction. The stream of 1,2-dichloroethane (and its pyrolysis products) and the fluid or the stream of particles are in contact for the period of time necessary to effect a significant conversion of the 1,2-dichloroethane. This period of contact time typically ranges from 0.010 to 0.5 second and preferably from 0.050 to 0.200 second.

It is also within the scope of the invention to add pyrolysis initiators such as, for example, chlorine or chlorine-donating compounds such as $CCl_4$, hexachloroethane or thionyl chloride, to the $D_{12}$ or to the stream of particles.

One skilled in this art can easily determine the amount of fluid or particles at high temperature, as well as such temperature, in order that the temperature remains sufficient during the contact time to effect said significant conversion.

The conversion increases in direct proportion to the temperature and the contact time.

The feedstream containing the 1,2-dichloroethane can be contacted with the fluid or the stream of particles at high temperature by means of a device such as a sprayer or two concentric tubes, the outlets of which are arranged such that the flows form an angle in order to be better mixed. This may also be accomplished via injectors disposed within a tube.

The pyrolysis reaction is terminated by quenching the reaction mixture, namely, the combined stream containing essentially the 1,2-dichloroethane (and its products of pyrolysis) and the fluid or stream of particles at high temperature. This quenching can be carried out using cold 1,2-dichloroethane.

The pyrolysis reaction is carried out, for example, in a single pipe and a flow of cold liquid 1,2-dichloroethane is injected into the outlet of the pipe, the total reaction mixture is then transferred into a gas/liquid separator and then the usual distillation operations are carried out in order to recover the vinyl chloride, the 1,2-dichloroethane, HCl, the transportation fluid or gas and the byproducts of pyrolysis.

If a stream of particles at high temperature has been used to heat the 1,2-dichloroethane, the particles can be separated from the reaction mixture by cycloning or any equivalent system before conducting the quenching.

In order to further illustrate the present invention and the advantages thereof, the following specific examples are given, it being understood that same are intended only as illustrative and in nowise limitative.

EXAMPLES 1 and 2

A reactor constituted by a horizontal tube fabricated from inconel was used. The 1,2-dichloroethane and very hot nitrogen were injected into one of the ends of such apparatus using a nozzle.

The nozzle was marketed under the trademark Sonicore Atomizers, model 052 MB1 by Sonic Development Corporation, 305 Island Road, Mahwah, N.J.

It was of the sprayer type, the 1,2-dichloroethane was injected into the center of which, into its axis, and then the hot nitrogen into the concentric outer chamber. In order to avoid a blockage by coke on the 1,2-dichloroethane side, a ceramic tubular sleeve was introduced to thermally isolate the 1,2-dichloroethane until it admixed with the nitrogen at the outlet of the nozzle.

The 1,2-dichloroethane was conveyed into the reactor via a peristaltic pump. The speed of rotation of the pump was adjusted and the weight of 1,2-dichloroethane injected was determined by virtue of a balance. This permitted calculating, by two different methods, the flow rate of 1,2-dichloroethane which passed through the reactor.

In this nozzle, welded to the inlet of the reactor, the 1,2-dichloroethane, heated beforehand to 100°–150° C., mixed with the heat-exchanging fluid (nitrogen) which provided it with the energy necessary to attain the desired reaction temperature.

At the outlet of the nozzle, the reaction began in the reactor (tube fabricated of inconel, having a diameter of 12.5 mm and a length of 825 mm) which was insulated by electrical heating tapes; the assembly being embedded in the heat insulator. A series of thermocouples arranged axially along the entire length of the reactor continuously monitored the temperature profile.

Depending on the strength of the heating tapes and the amount of 1,2-dichloroethane converted, it was possible to supply this small-sized apparatus with more heat than that consumed by the endothermic pyrolysis.

At the reactor outlet, two nitrogen jets at room temperature suddenly cooled the reaction mixture to below 400° C. to immediately terminate pyrolysis of the 1,2-dichloroethane.

These gases were then mixed with methane (whose flow rate was controlled) which served the function of tracer and made it possible to carry out material balances from the chromatographic analyses.

Then, they were cooled a second time via two water exchangers to room temperature. The liquid fraction was collected in a round-bottomed flask (condensation of the heavier hydrocarbons). The gaseous fraction was transferred through, in a first step, a water column where the HCl was trapped, and then a column charged with active charcoal where the VCM (vinyl chloride) was trapped, and was then expelled into the atmosphere.

The products of the reaction were analyzed by gas phase chromatography.

All of the information monitored by the sensors of the pilot plant, such as the temperature profile in the reactor, the nitrogen and 1,2-dichloroethane flow rates, the pressure in the reactor, and the like, were permanently recorded by a computer. This permitted determination of such parameters over time.

At the end of each experiment, the reactor was purged with nitrogen to prevent the formation of an explosive mixture.

The results of Examples 1 and 2 are reported in Table 1.

In said Table 1, T1 denotes the temperature attained by the 1,2-dichloroethane as soon as it was mixed with the nitrogen.

T2 denotes the average temperature of the reaction mixture in the reactor.

The pressure is in bars absolute.

The conversion denotes the percentage of 1,2-dichloroethane which had been pyrolyzed.

The selectivity towards vinyl chloride indicates the percentage of the pyrolyzed 1,2-dichloroethane which was converted into vinyl chloride, and similarly for the other products.

EXAMPLE 3 ( Comparative )

The pyrolysis of 1,2-dichloroethane was carried out in an oven of the prior art (Ullmann's). The 1,2-dichloroethane was at 100° C. at the inlet of the oven, then it was heated, vaporized and heated to 480° C. The results are also reported in Table 1:

TABLE 1

|  | Example 1 | Example 2 | Example 3 (Comparative) |
|---|---|---|---|
| Experimental parameters: |  |  |  |
| Inlet temperature (T1) of the reactor (°C.) | 480 | 570 | — |
| Mean temperature (T2) (°C.) | 509 | 540 | 480 |
| Passage time based on T2 (ms) | 181 | 154 | 20000 |
| Nitrogen/D12 dilution (molar) | 9 | 35 | — |
| Total pressure in bars absolute | 1.2 | 1.4 | 16 |
| Surface/Volume ratio of the reactor (cm$^{-1}$) | 3.2 | 3.2 | 0.4 |
| Material of the reactor | Inconel 600 | Inconel 600 | Alloyed steel |
| Conversion of the 1,2-dichloroethane (%) | 8.4 | 63.6 | 56 |
| Selectivity: |  |  |  |
| Acetylene | 0 | 1.18 | 0.197 |
| Ethylene | 1.77 | 1.21 | 0.015 |
| Vinyl chloride | 97.38 | 95.62 | 97.93 |
| Ethyl chloride | 0 | 0 | 0.01 |
| 1,1-Dichloroethylene | 0.03 | 0.33 | 0.009 |
| Dichloromethane | 0 | 0 | — |
| trans-1,2-Dichloroethylene | 0.14 | 0.12 | — |
| 1,1-Dichloroethane | 0.37 | 0.10 | 0.117 |
| Chloroprene | 0 | 1.04 | 0.111 |
| cis-1,2-Dichloroethylene | 0.30 | 0.19 | — |
| Chloroform | 0 | 0.01 | 0.004 |
| 1,1,1-Trichloroethane | 0 | 0 | — |
| Carbon tetrachloride | 0 | 0 | — |
| Trichloroethylene | 0 | 0.01 | 0.046 |
| 1,2-Dichloropropane | 0 | 0 | — |
| cis-1,2-Dichloropropene | 0 | 0.01 | — |
| trans-1,3-Dichloropropene | 0 | 0 | — |
| 1,1,2-Trichloroethane | 0.20 | 0.12 | 0.019 |
| Tetrachloroethylene | 0 | 0.02 | 0.044 |
| Chlorobenzene | 0 | 0.01 | 0.038 |
| 1,1,2,2-Tetrachloroethane | 0 | 0.01 | 0.046 |
| 1,3-Dichlorobenzene | 0 | 0.01 | — |
| 1,4-Dichlorobenzene | 0 | 0.00 | — |
| 1,2-Dichlorobenzene | 0 | 0.00 | — |

EXAMPLES 4 AND 5

The reaction was carried out as in Examples 1 and 2, but employing higher temperatures and shorter contact times.

The results are reported in Table 2.

EXAMPLE 6

The same inconel tube was used as in the above examples, but without the mixing nozzle and the tube was arranged vertically. Above the tube was situated another tube of greater diameter connected to the reactor tube by a cone and employed to mix the sand and the 1,2-dichloroethane. Above this mixer a reservoir was disposed containing silica sand of a 100 micron particle size heated to 1100° C.

The mixer was supplied with a mixture of nitrogen and 1,2-dichloroethane, and this flow rate and optionally that of the sand were adjusted to provide a temperature of the gas (i.e., of the 1,2-dichloroethane) at the inlet of the inconel reactor tube at from 550° to 650° C.

The residence time of the 1,2-dichloroethane in the mixer way negligible, considering the residence time in the inconel tube.

There was arranged, at the outlet of the inconel tube, a cylindrical reservoir having a diameter of 13 cm and a height of 26 cm for separating the sand from the gases. Quenching was carried out by means of a jet of cold nitrogen.

The same results as in Example 5 were obtained.

TABLE 2

|  | Example 4 | Example 5 |
|---|---|---|
| Experimental parameters: |  |  |
| Inlet temperature (T1) of the reactor (°C.) | 650 | 678 |
| Mean temperature (T2) (°C.) | 662 | 677 |
| Passage time based on T2 (ms) | 89 | 94 |
| Nitrogen/D12 dilution (molar) | 9 | 9.8 |
| Total pressure (bars absolute) | 1.5 | 1.5 |
| Surface/Volume ratio of the reactor (cm$^{-1}$) | 3.2 | 3.2 |
| Material of the reactor | Inconel 600 | Inconel 600 |
| Conversion of the 1,2-dichloroethane (%) | 77.0 | 86.6 |
| Selectivity: |  |  |
| Acetylene | 1.52 | 2.42 |
| Ethylene | 1.74 | 2.09 |
| Vinyl chloride | 95.54 | 92.63 |
| Ethyl chloride | 0.00 | 0.00 |
| 1,1-Dichloroethylene | 0.65 | 0.73 |
| Dichloromethane | 0.01 | 0.01 |
| trans-1,2-Dichloroethylene | 0.10 | 0.08 |
| 1,1-Dichloroethane | 0.14 | 0.13 |
| Chloroprene | 0.27 | 2.17 |
| cis-1,2-Dichloroethylene | 0.16 | 0.12 |
| Chloroform | 0.01 | 0.00 |
| 1,1,1-Trichloroethane | 0.00 | 0.00 |
| Carbon tetrachloride | 0.01 | 0.01 |
| Trichloroethylene | 0.02 | 0.01 |
| 1,2-Dichloropropane | 0.00 | 0.00 |
| cis-1,2-Dichloropropene | 0.00 | 0.00 |
| trans-1,3-Dichloropropene | 0.00 | 0.00 |
| 1,1,2-Trichloroethane | 0.07 | 0.06 |
| Tetrachloroethylene | 0.08 | 0.06 |
| Chlorobenzene | 0.01 | 0.05 |
| 1,1,2,2-Tetrachloroethane | 0.00 | 0.00 |
| 1,3-Dichlorobenzene | 0.00 | 0.01 |
| 1,4-Dichlorobenzene | 0.00 | 0.01 |
| 1,2-Dichlorobenzene | 0.00 | 0.00 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of vinyl chloride, comprising intimately contacting, in the absence of steam, a feedstream of 1,2-dichloroethane with a heated flow of solid particulates capable of providing sufficient heat exchange to flash transfer a dehydrochlorinating amount of thermal energy to said 1,2-dichloroethane and thereby ultrapyrolyzing at least a fraction of same into vinyl chloride and HCl, and recovering said vinyl chloride from the medium of ultrapyrolysis, wherein said heated flow of fluid or solid particulates is heated before coming into contact with said feedstream of 1,2-dichloroethane where said solid particulates are silica, corundum-type alumina or attapulgite silicoaluminates.

2. The process as defined by claim 1, further comprising quenching the medium of ultrapyrolysis upstream of recovering said vinyl chloride therefrom.

3. The process as defined by claim 1, further comprising intimately contacting said feedstream of 1,2-dichloroethane with a flow of hot gas.

4. The process as defined by claim 1, further comprising intimately contacting said feedstream of 1,2-dichloroethane with a flow of hot nitrogen, methane, ethylene, benzene or HCl.

5. The process as defined by claim 1, said heated flow of solid particulates having a particle size ranging from 10 to 500 microns.

6. The process as defined by claim 5, said heated flow of solid particulates having a particle size ranging from 10 to 40 μm.

7. The process as defined by claim 1, said heated flow of solid particulates being entrained in a transport gas.

8. The process as defined by claim 1, said feedstream consisting essentially of 1,2-dichloroethane.

9. The process as defined by claim 1, said contacting is for a period of contact time ranging from 0.010 to 0.5 second.

10. The process as defined by claim 9, said period of contact time ranging from 0.05 to 0.2 second.

11. The process as defined by claim 1, said medium of ultrapyrolysis comprising a pyrolysis initiator.

12. The process as defined by claim 1, the temperature of ultrapyrolysis being at least 480° C.

13. The process as defined by claim 12, said temperature of ultrapyrolysis ranging from 550° to 750° C.

14. The process as defined by claim 13, said temperature of ultrapyrolysis ranging from 550° to 650° C.

15. The process as defined by claim 1, carried out in a tubular reactor.

* * * * *